United States Patent
Fox et al.

(10) Patent No.: US 9,486,643 B2
(45) Date of Patent: Nov. 8, 2016

(54) METHODS, SYSTEMS AND COMPUTER READABLE STORAGE MEDIA STORING INSTRUCTIONS FOR IMAGE-GUIDED TREATMENT PLANNING AND ASSESSMENT

(71) Applicant: EMORY UNIVERSITY, Atlanta, GA (US)

(72) Inventors: Timothy H. Fox, Atlanta, GA (US); Eduard Schreibmann, Decatur, GA (US)

(73) Assignee: Emory University, Atlanta, GA (US)

( * ) Notice: Subject to any disclaimer, the term of this patent is extended or adjusted under 35 U.S.C. 154(b) by 218 days.

(21) Appl. No.: 14/100,584

(22) Filed: Dec. 9, 2013

(65) Prior Publication Data

US 2014/0163302 A1    Jun. 12, 2014

Related U.S. Application Data

(60) Provisional application No. 61/734,511, filed on Dec. 7, 2012, provisional application No. 61/790,325, filed on Mar. 15, 2013.

(51) Int. Cl.
  *G06K 9/00* (2006.01)
  *A61N 5/10* (2006.01)

(52) U.S. Cl.
  CPC .................... *A61N 5/1031* (2013.01)

(58) Field of Classification Search
  USPC ................................................ 382/128–134
  See application file for complete search history.

(56) References Cited

U.S. PATENT DOCUMENTS

| | | | | |
|---|---|---|---|---|
| 2001/0021269 A1* | 9/2001 | Inoue | ..................... | G06T 5/009 382/169 |
| 2005/0096515 A1* | 5/2005 | Geng | .................... | A61N 5/1049 600/315 |
| 2007/0014456 A1* | 1/2007 | Ramamurthy | ........ | G06T 7/0012 382/128 |
| 2009/0262894 A1* | 10/2009 | Shukla | ................. | A61N 5/1049 378/65 |

OTHER PUBLICATIONS

Badea et al. "A registration based approach for 4D cardiac micro-CT using combined prospective and retrospective dating." Medical Physics, 2008; 35(4): 1170-1179.
Fox et al. "SU-FF-J-122: Deformable Image Registration Using FDG-PET/MRI for Metastatic Breast Cancer Detection." Medical Physics, 2007; 34: 2396.

(Continued)

*Primary Examiner* — Alex Liew
(74) *Attorney, Agent, or Firm* — Emory Patent Group

(57) ABSTRACT

Methods, systems and computer-readable storage media relate to image-guided treatment planning and treatment assessment. The methods, systems, and the computer-readable storage medias according to embodiments can analyze treatment response and can determine an accurate, outcome-based response assessment of treatment (e.g., radiation treatment). The methods may include a method for determining a treatment response. The method may include registering at least a first image data and a second image data of a subject, the first image data corresponding to a first time point, the second image data corresponding to a second time point, the first time point and the second time point being different with respect to a treatment session and/or treatment stage. The method may include processing the registered image to determine a treatment response. The registering may be based on deformable registration.

20 Claims, 12 Drawing Sheets

(56) References Cited

OTHER PUBLICATIONS

Fox et al. "TU-C-332-02: Concomitant Segmentation and Registration of Liver Anatomy Using SPECT-CT Imaging." Medical Physics, 2008; 35: 2894.

Li et al. "Model-based image reconstruction for four-dimensional PET." Medical Physics, 2006; 33(5): 1288-1298.

Perona et al. "Scale-Space and Edge Detection Using Anisotropic Diffusion." IEEE Transactions on Pattern Analysis and Machine Intelligence, 1990; 12(7): 629-639.

Sarfaraz et al. "Radiation absorbed dose distribution in a patient treated with yttrium-90 microspheres for hepatocellular carcinoma." Medical Physics, 2004; 31(9): 2449-2453.

Schriebmann et al. "Quantification of Tumor Response in Serial PET Imaging Using Level Set Clustering." AAPM Joint Imaging-Therapy General Poster, 2010.

Schriebmann et al. "SU-GG-J-147: Quantification of Tumor Response in Serial PET Imaging Using Level Set Clustering." Medical Physics, 2010; 37: 3179.

Schriebmann, E. "TH-A-224-01: Automated Segmentation through Deformable Registration." Medical Physics, 2011; 38: 3840.

Schriebmann et al. "TU-C-211-1: Thoracic and Abdominal Atlas Segmentation with Diffeomorphic Multi-Modality Registration." Medical Physics, 2011; 38: 3762.

Schriebmann et al. "Towards automated planning for unsealed source therapy." Journal of Applied Clinical Medical Physics, 2012; 13(4): 23-35.

Schriebmann et al. "SU-E-J-189: The Kullback-Leiber Divergence for Quantifying Changes in Radiotherapy Treatment Response." Medical Physics, 2012; 39: 3696.

Schriebmann, E. "TN-A-211-01: Deformable Registration in the Clinic: From Commissioning to Advanced Applications." Medical Physics, 2012; 39: 3979.

Schriebmann et al. "Voxel clustering for quantifying PET-based treatment response assessment." Medical Physics, 2013; 40(1): 012401-1-012401-12.

Schriebmann et al. "Multiatlas segmentation of thoracic and abdominal anatomy with level set-based local search." Journal of Applied Clinical Medical Physics, 2014; 15: 22-38.

Yang et al. "Evaluation of on-board kV cone beam CT (CBCT)-based dose calculation." Physics in Medicine and Biology, 2007; 52: 685-705.

* cited by examiner

METHODS, SYSTEMS AND COMPUTER READABLE STORAGE MEDIA STORING INSTRUCTIONS FOR IMAGE-GUIDED TREATMENT PLANNING AND ASSESSMENT

CROSS REFERENCE TO RELATED APPLICATIONS

This application claims priority to Provisional Application Ser. No. 61/790,325 filed Mar. 15, 2013 and Provisional Application Ser. No. 61/734,511 filed Dec. 7, 2012, which are hereby incorporated by reference in their entirety.

BACKGROUND

Imaging has become more crucial in managing treatment options for cancer patients. Imaging can be an extremely powerful tool because it allows for personalized treatment assessment. Imaging can be used to detect and quantify tumor response, as well as assess therapeutic targets.

However, current treatment response assessment methods and systems do not accurately and efficiently determine personalized absorbed dose estimates of targeted radiotherapy. This can be essential to establish fundamental dose-response relationships for efficacy and toxicity and thus treatment planning. Additionally, current approaches used to assess treatment response do not completely capture a tumor's response.

SUMMARY

Thus, there is a need for accurate and efficient imaging processes for treatment planning and treatment response assessment.

The disclosure relates to systems, methods, and computer-readable media storing instructions for treatment planning and treatment assessment. In some embodiments, the disclosure may relate to a method for analyzing an image-guided treatment therapy for a subject. The method may be performed any time before, during, and/or after treatment and/or planning (e.g. pre or post-treatment; and/pre-post planning).

In some embodiments, the method may include registering at least a first image data and a second image data of a subject, the first image data corresponding to a first time point, the second image data corresponding to a second time point, the first time point and the second time point being different respect to a treatment session and/or treatment stage; analyzing registered image to evaluate dosage plan; and outputting results. In some embodiments, the registering can be deformable registration.

In some embodiments, the disclosure may relate to a method for determining a treatment response of a treatment for a region of interest. In some embodiments, the method for determining a treatment response may include registering at least a first image data and a second image data of a region of interest. The first image data may corresponding to a first time point and the second image data may correspond to a second time point, and the first time point and the second time point may be different with respect to a session and/or treatment stage.

In some embodiments, the method may include determining a treatment response, by a computer having a processor and a memory, based on at least the registered image, treatment plan information associated with the treatment, or a combination thereof. The determining may include processing the registered image to determine a difference image; and processing at least the difference image to determine one or more signal regions, each signal region corresponding one or more voxels that are grouped together based on location and signal value. In some embodiments, the determining may include determining a treatment response associated with the signal value of the one or more signal regions, a positive signal region indicating a treatment-resistant region and a negative signal region indicating a respondent region. The one or more signal regions may include one or more positive signal regions, one or more negative signal regions, or a combination thereof. The method may include outputting treatment response results.

In some embodiments, the disclosure may relate to a method of determining a treatment response. In some embodiments, the method may include registering at least a first image data and a second image data of a region of interest. The first image data may correspond to a first time point, the second image data may correspond to a second time point, and the first time point and the second time point may be different with respect to a session and/or treatment stage. The methods may include determining a dose for each of voxel of the first image data and the second image data.

In some embodiments, the method may include determining a treatment response, by a computer having a processor and a memory, based on at least the registered image. The determining may include determining a sum dose distribution using the registered image by adding the dose associated with each voxel of the first image data to each corresponding voxel of the second image data. The method may include outputting treatment response results.

In some embodiments, the stages include pre-treatment, pre-treatment planning, post-treatment planning, and post-treatment. In some embodiments, the first data may correspond to pre-treatment and the second data corresponds to one of pre-planning, post-planning, and/or post-treatment. In some embodiments, the image data may include PET, MR, CT, SPECT-CT, or a combination thereof.

In some embodiments, the method may include receiving the image data.

In some embodiments, the method may include receiving at least one of planning dose or planning contours associated with the image data. In some embodiments, the results include treatment response.

In some embodiments, the disclosure may relate to a method that includes processing at least a first image data and a second image data of a subject, the first image dataset and the second image data set being different; and generating dose-volume histograms. The processing may include registration. The registration may be deformable registration, In some embodiments, the first image data may be associated with a first time point and the second image data may be associated with a second time point, the first time point and the second time point being different respect to a treatment and/or treatment planning.

In some embodiments, the method(s) may be an automatic method. In some embodiments, the method(s) may be performed by a computer having a memory and a processor. In some embodiments, the disclosure may include a system having a memory and processor capable of performing the method(s), according to embodiments.

In some embodiments, the disclosure may relate to a computer-readable medium. The computer readable medium may store instructions for analyzing an image-guided treatment therapy for a subject. The computer readable medium may be a non-transient medium. The instructions may include registering at least a first image data and a second image data of a subject, the first image data corresponding to a first time point, the second image data corresponding to a second time point, the first time point and the second time point being different respect to a treatment and/or treatment planning; and determining a treatment response based on at least the registered image. In some embodiments, the treatment response may include analyzing registered image to evaluate dosage plan; and outputting results. In some embodiments, the registering may be deformable registration.

In some embodiments, the disclosure may relate to a system. The system may include an processor and a memory, the processor configured to cause: registering at least a first image data and a second image data of a subject, the first image data corresponding to a first time point, the second image data corresponding to a second time point, the first time point and the second time point being different with respect to a session and/or treatment stage; determining a treatment response; and outputting results. In some embodiments, the determining a treatment response may include analyzing registered image to evaluate dosage plan. In some embodiments, one of the image data may be received in substantially real-time.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
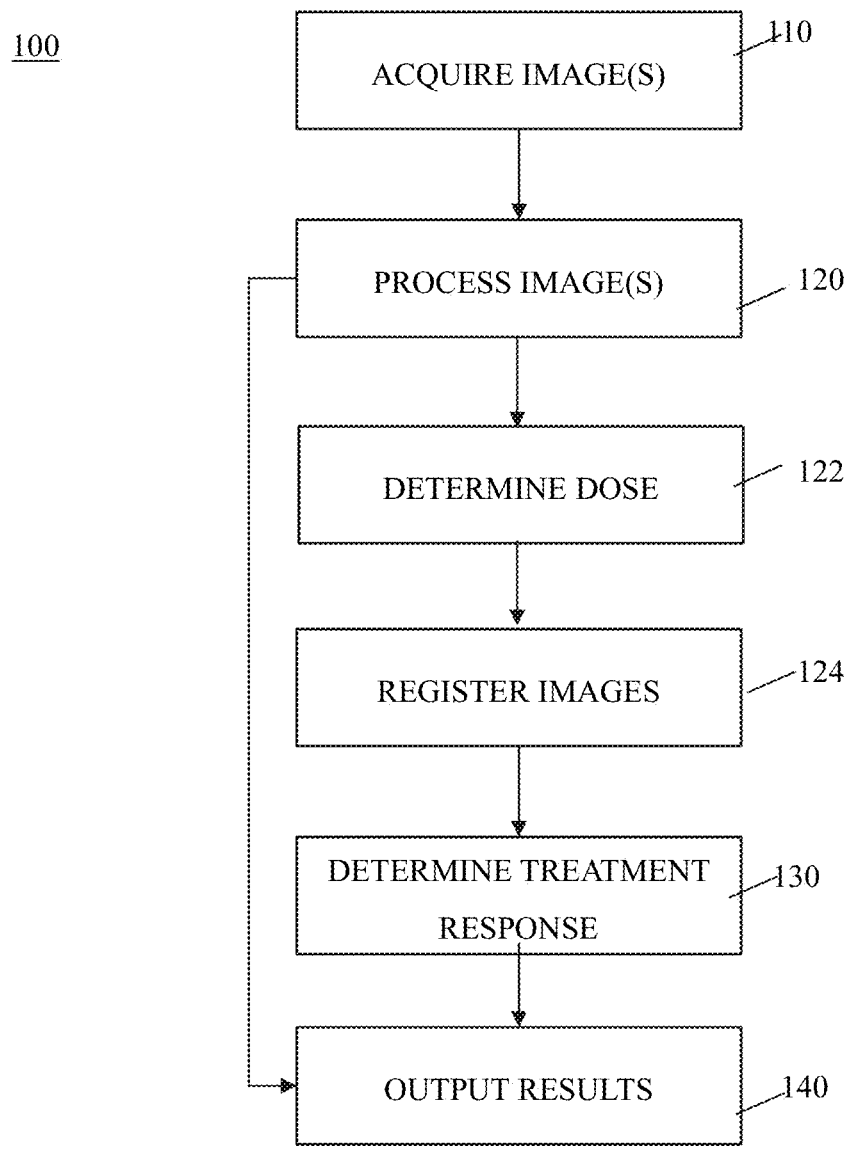
FIG. 1 shows a method of determining treatment response according to some embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The methods, systems, and the computer-readable storage media relate to treatment planning and treatment assessment. The methods, systems, and the computer-readable storage media according to embodiments can analyze treatment response and can provide an accurate, outcome-based response assessment of treatment (e.g., radiation treatment). The disclosure can enhance detectability of residual tumor, for example, by detecting, analyzing, and guiding the physician toward suspicious regions. Additionally, the disclosure can also correlate biological changes extracted from the data with planning information for an identification of successful or unsuccessful treatments.

The methods, systems, and computer readable storage media may be used to assess the effectiveness of therapy treatment (e.g., chemotherapy) in substantially real-time, even before the first cycle is complete. This can allow for adjustment of dose and chemotherapy agent, sparing patients unnecessary side effects.

Methods

The methods of the disclosure are not limited to the steps described herein. The steps may be individually modified or omitted, as well as additional steps may be added.

Unless stated otherwise as apparent from the following discussion, it will be appreciated that terms such as "averaging," "binarizing," "filtering," "combining," "reconstructing," "segmenting," "generating," "registering," "determining," "obtaining," "processing," "computing," "selecting," "estimating," "detecting," "tracking," "outputting," "applying," "classifying," "calculating" "receiving," "acquiring," "evaluating," "analyzing," "summarizing," "comparing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

FIG. 1 illustrates a method 100 according to embodiments to process image data for at least two different time points (e.g., different sessions and/or staged procedures) to determine a treatment response. By way of example, the method 100 may process image data for at least two different time points with respect to treatment and/or treatment planning stages, for example, for pre-treatment planning and/or post-treatment assessment.

In some embodiments, the method 100 may include a step of acquiring at least one set of image data of a region of interest for a time point. The image data may include image(s) acquired by any imaging modality. In some embodiments, the image data for a time point may include image data acquired by at least one imaging modality. In some embodiments, the image data for a time point may include image data acquired by more than one imaging modality.

For example, the image data for a time point may be image data acquired by, for example, positron emission tomography (PET), magnetic resonance imaging (MRI), computed tomography (CT), single-photon emission computed tomography (SPECT), or any combination thereof. For example, the image data may include but is not limited to PET image data, MRI image data, CT data, SPECT image data, or a combination thereof. In some embodiments, the image data for each time point may each include SPECT-CT image data.

In some embodiments, the image data may be acquired directly from the imaging modality device. In other embodiments, the image data may be acquired from a database, for example, provided on the network. In some embodiments, each data set may be formatted and saved according to DICOM protocol.

In some embodiments, the image data may be for any time point of the treatment procedure. In some embodiments, the time point may correspond to a session during a stage of the treatment. The stages of treatment may include but are not limited to pre-treatment, pre-treatment planning, post-treatment planning and post-treatment. The image data may be acquired during any one or a combination of time points between and including pre-treatment planning and post-treatment stages. In this way, the image data may have been acquired during any of the following: pre-treatment imaging, pre-treatment planning imaging, post-treatment planning imaging, post-treatment imaging, and/or any combination thereof.

In some embodiments, the image data may be acquired for at least two different time points (e.g., a first time point, a second time point, a third time point, a fourth time point, etc.). In other embodiments, the image data may be acquired for more than two different time points.

In some embodiments, the image data may be acquired for sessions of different treatment stages, different sessions of a stage, or any combination thereof. In further embodiments, the image data may include data acquired for additional and/or different time points.

For example, image data may be acquired for any session of a treatment stage. In this example, the time points may be acquired for any session of the following treatment stages: pre-treatment, pre-planning, post-planning, post-treatment, or a combination thereof. In some embodiments, pre-treatment imaging, pre-treatment planning image, post-treatment planning imaging and post-treatment imaging may generally correspond to a first time point, a second time point, a third time point, and a fourth time point.

In another example, image data may be acquired for different sessions of a treatment stage. By way of example, image data may be acquired for at least two different sessions during the post-treatment planning stage.

In some embodiments, the method 100 may include a step 120 of processing the image data, for example, for each time point. In some embodiments, the image data for a time point acquired in step 110 may need to be processed, for example, if the image data for a time point includes image data from multiple imaging modalities (e.g., CT and SPECT). For example, image data for more than one modality for a specific time point may be processed so that it may be comparable to image data for a different time point. In some embodiments, this method may be omitted. For example, the image data for a time point that include image data from different imaging modalities (e.g., CT and SPECT) may have been previously registered.

Figure 2A:
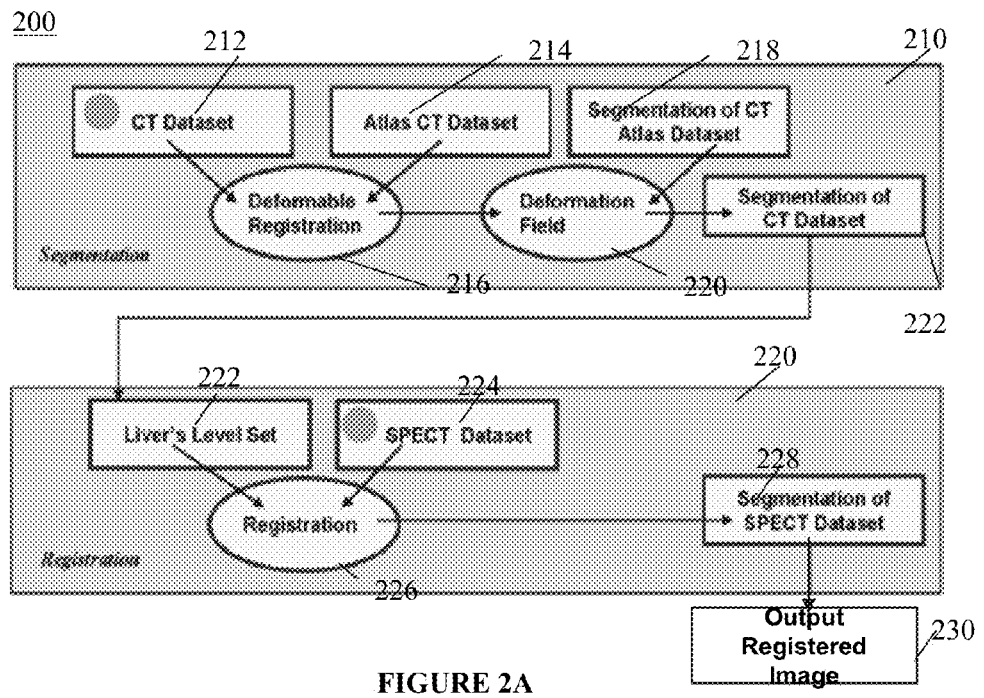
FIG. 2A shows a method of processing image data according to some embodiments.

FIG. 2A shows a method 200 of registering image data from multiple imaging modalities for a specific time point, according to embodiments. In some embodiments, the received image data may be previously, automatically processed according to this method. In some embodiments, the method 200 may be used by itself to automatically process the received image data, for example, for determining a treatment plan. Also, in other embodiments, the received image data may be processed by another method. Although the registration and segmentation processes for treatment planning in method 200 incorporate SPECT datasets and use algorithms customized to the specifics of SPECT-CT imaging datasets, the approach may be modified for other imaging datasets. Additionally, the method 200 refers to image data set of a liver of a subject, but the region of interest is not limited to a liver. It may be any region of interest of a subject. For example, the region of interest may include brain, head and neck, thoracic or abdominal anatomy.

It will be noted in FIG. 2A (only), the rectangles represent data (input and output) and the ellipses represent procedures. The data illustrated may be, for example, received, acquired, stored, generated, outputted, or combination thereof. For example, the data may be received and/or acquired from a memory storage and/or another device (e.g., image acquisition system).

The method generally combines information from the segmentation and registration procedures into a common robust approach that can simplify the task. In this method, tedious manual segmentation can be replaced with structure identification through atlas registration that relies on an improved demons algorithm in which iterations are updated in a diffeomorphic space to account for large interpatient variations. Also, the rigid registration method according to the disclosure may be based on a hybrid approach combining advantages of the contour and voxel-based approaches and thus can accurately register anatomical and functional imaging data of the abdominal anatomy.

As shown in FIG. 2A, the method 200 may include a step 210 of segmentation. The segmentation step 200 may be an atlas segmentation approach. The segmentation step 210 may include receiving image data set of a subject (referred to as "subject dataset") (e.g., CT) (step 212) and an atlas image data set (e.g., CT image data) (step 214). The atlas image data set (FIG. 2A) may be a stored template CT of a representative or average patient in which the clinical structures have been delineated by an expert. Next, using deformable registration, the atlas image data set may be matched to the subject dataset (step 216). The deformable registration may deduce a one-to-one correspondence between the two CT datasets. This registration technique can also have the ability to cope with large differences customized for CT datasets and with quick running speeds (e.g., few minutes).

In some embodiments, the deformable registration may extend the demons formulation, which warps the input images according to local characteristics with forces inspired from the optical flow equations. The deformable registration may use a nonparametric diffeomorphic image registration algorithm that uses an exponential update of the deformation field. This can result in significant accuracy improvement over the classical demons formulation, based on the algorithm's ability to cope with large deformations between patients.

In some embodiments, the following settings may be used with deformable registration: a step size of about 2; a sigma value for the deformation field of 1; and 0.2 for the update field. Additionally, the data may be preprocessed. For preprocessing, both the template and the patient datasets, may be smoothed using an edge-preserving gradient anisotropic diffusion filter implementing the classical Perona-Malik approach. See, e.g., Perona P et al. Scale-space and edge detection using anisotropic diffusion. IEEE Trans Pattern Anal Mach Intell. 1990; 12(7):629-639. A histogram filter may be used before the registration to compensate for differences in HU calibration should the images come from different scanners. To speed up the registration and decrease the chance of it being trapped in a local minima, a multi-resolution approach may be used where images were registered first at a coarse level and then the result was used to initialize a full resolution registration. For example, a 2-stage multiresolution approach may be used with 50, 40, and 20 iterations for each resolution.

The segmentation of the CT atlas dataset (step 218) may then be warped with the deformation field (step 220) resulting from the registration to produce an automated segmentation of the (received) subject dataset (step 222).

Next, the segmented subject data set and a SPECT image dataset may be registered (step 220). The registration may be a narrow band registration. Narrow band registration (step 226) may be used to connect a liver segmentation in the (received) CT dataset (step 222) to the corresponding gradients of voxel activity in the SPECT images (224). The aim can be to disregard interior liver voxels that are too non-uniform in intensities to allow reliable use of classical MI setups.

The narrow band—a signed distance around an object of interest such as the liver—may be used as optimization criteria to constrain the registration to relevant features without relying on the user's segmentation accuracy. As compared to pure intensity-based registration metrics, the narrow band approach can ignore irrelevant regions such as background and noise, as the metric is computed only on the pixels within the signed distance. However, the method may not be as sensitive to segmentation as pure edge feature-based methods, because the signed distance represents a transition zone around the edges that compensates for inaccuracies in the initial segmentation. For example, for the SPECT-CT registration, the module can be designed to fit the segmentation of a region of interest (e.g., liver) with the steepest gradient in the SPECT dataset (step 228). Settings, for example, may be a narrow band width of 10 mm and a regular step gradient optimizer with a maximum step of 2.

The registration method can have advantages over other methods because (a) it is completely automated, as it does not require mask of the liver in both datasets; (b) it can increase accuracy, as it matches a segmentation to the gradients directly, without the use of user-delineated masks in both images; (c) it can increase speed, as the normal cross-correlation (NCC) metric permits use of fast gradient-based algorithms rather than the time-consuming simulated annealing optimization algorithm; and d) it does not critically depend on the CT-based segmentation accuracy, as narrow band itself defines an error margin around the initial segmentation.

Next, the method 200 may include a step 230 of outputting the registered image for a time point. In some embodiments, the outputting may include but is not limited to displaying the image(s), printing the image(s), and storing the image(s) remotely or locally. In other embodiments, the image(s) may be forwarded for further processing, for example, for registering to image data of a different time point.

In some embodiments, the method 100 may include a step 122 of determining the absorbed dose by the region of interest for the session corresponding to the time point. In some embodiments, the dose may be determined for the image data received for one, some, or all time points. In the cases, for example, where the image data includes image data for different time points during a treatment stage (e.g., post-planning treatment stage), the dose calculation may be performed for each set of image data. In some embodiments, this step may be omitted.

Figure 2B:
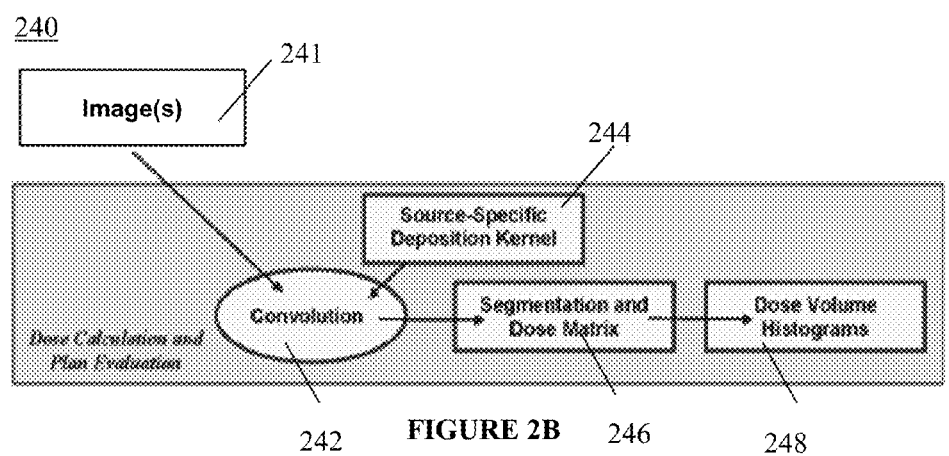
FIG. 2B shows a method of determining a dose calculation according to some embodiments.

In some embodiments, the dose may be determined by a method 240 shown in FIG. 2B. In other embodiments, the dose may be determined according to other known methods.

As shown in FIG. 2B, the image data (e.g., acquired in step 110 and/or processed in step 120) for a time point may be processed to determine at least dose calculation (step 241). In some embodiments, the method 240 may include a convolution step 242 to determine dose distribution for the image data for a time point. For example, for SPECT image, the dose calculation model may be implemented as a convolution operation of the of the $^{90}Y$ SPECT cumulated activity concentration map with yttrium-90 deposition kernels (e.g., the published $^{90}Y$ Monte Carlo dose deposition kernels; see, e.g., Sarfaraz M et al. Radiation absorbed dose distribution in a patient treated with yttrium-90 microspheres for hepatocellular carcinoma, *Medical Physics* 2004; 31:2449-2453) to create a 3D absorbed distribution associated with each $^{90}Y$ radio embolization (steps 242 and 244). The absorbed dose calculation can assume complete deposition of a dose administered with no biologic clearance.

In some embodiments, the resulting dose distribution may then be combined with the anatomical information to compute dose volume statistics (e.g., dose-volume histograms) for target and critical organs (Steps 246 and 248). In some embodiments, the dose distribution and/or dose-volume histograms may be further processed to produce patient-specific volumetric dose calculations and/or determine a treatment response (e.g., step 130). In further embodiments, this information may be used for radiation therapy treatment planning and/or treatment response analysis. In some embodiments, the dose distribution and/or the dose-volume histograms may then be outputted (for example, according to any of the methods discussed in step 140).

Figure 3A:
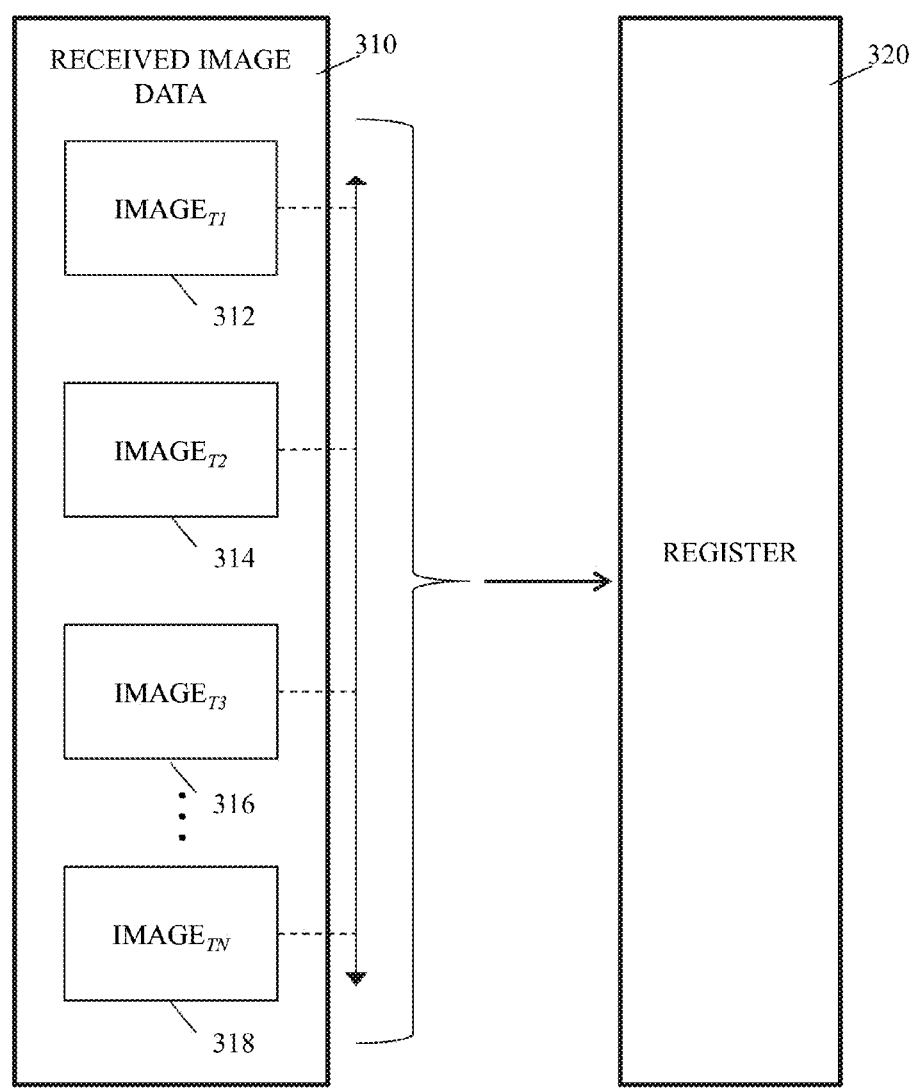
FIGS. 3A-3C show a method of registering image datasets according to some embodiments.

As shown in FIG. 1, the method 100 may include a step 124 of registering image data acquired from at least two different time points. FIG. 3A shows an example of a method 300 of registration, according to embodiments.

As shown in FIG. 3A, any combination of the image data from any time point may be received for registering (step 310). For example, the image data may be for any time point (e.g., T1, T2, T3 through TN) between and including a first session or pre-treatment through the last session or post-treatment. The image data may be for sessions of different treatment stages, different sessions of a stage, or any combination thereof.

In some embodiments, image data may be received from at least two different time points. It will be understood that the image data may be for at least two different time points (e.g., at least T1 and T2) and does not necessarily include all time points (e.g., T3 through TN) shown in FIG. 3. By way of example, image data may be received for a session during pre-treatment (e.g., pre-treatment image) and a session during post-treatment (e.g., post-treatment image). In other embodiments, image data for more than two different time points may be received. For example, image data for three different time points, four different time points, and more than four different time points may be received to be registered. In some embodiments, any of the image data received may be processed according to method 200. In other embodiments, the image data may be processed by other processing techniques.

Next, in step 320, image data for at least two different time points may be registered. The image data may be registered by any method. In some embodiments, the registration may be a deformable registration. This approach can eliminate differences resulting from patient positioning within the scanner at these different time points.

In some embodiments, the deformable image registration may map anatomical data into a common coordinate system and establish a one-to-one correlation between voxels in the two images, thereby removing motion and patient setup inaccuracies between the two datasets acquired at different time points.

Figure 3B:
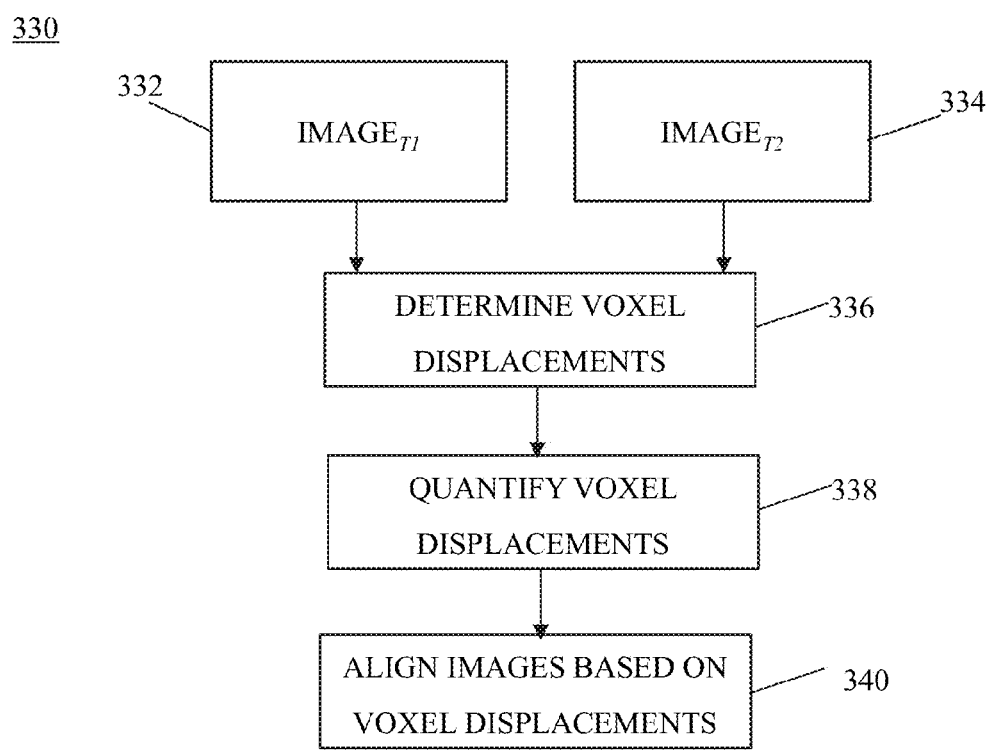

FIGS. 3B and C show a method of registering images using deformable registration, according to embodiments. The deformable registration may use multi-resolution free-form deformations based on cubic spline interpolation between sparse, uniformly distributed control points as its transformation model. Deformable image registration using multi-resolution free-form has been previously described. See, e.g., Badea C T, et al. A registration based approach for 4d cardiac micro-ct using combined prospective and retrospective gating. *Medical Physics* 2008; 35:1170-1179; Li T, et al. Model-based image reconstruction for four-dimensional pet. *Medical Physics* 2006; 33:1288-1298; and Yang Y, et al. Evaluation of on-board kilovoltage (kV) cone-beam CT (CBCT)-based dose calculation. *Physics in Medicine and Biology* 2007; 52:685-705. It will be understood that other deformable registration methods, as well as other methods, may be used to register images for different time points.

FIG. 3B shows a method 330 of registering image data from two different time points, according to embodiments. It will be understood that method is not limited to registering two time points and more than two different time points may be registered according to embodiments.

As shown in FIG. 3B, image data for a first time point (T1) and image data for a second time point (T2) may be received for registering (steps 332 and 334). By way of an example, T1 may correspond to image data for a session during the pre-treatment stage of a patient (e.g., pre-treatment image) and T2 may correspond to image data for a session during the post-treatment stage of the patient (e.g., post-treatment image). In some embodiments, the image data for each time point may include PET image data.

Next, the method 330 may include a step 340 of determining voxel displacements. In some embodiments, voxel displacements may be determined according to a method 350 shown in FIG. 3C.

Figure 3C:
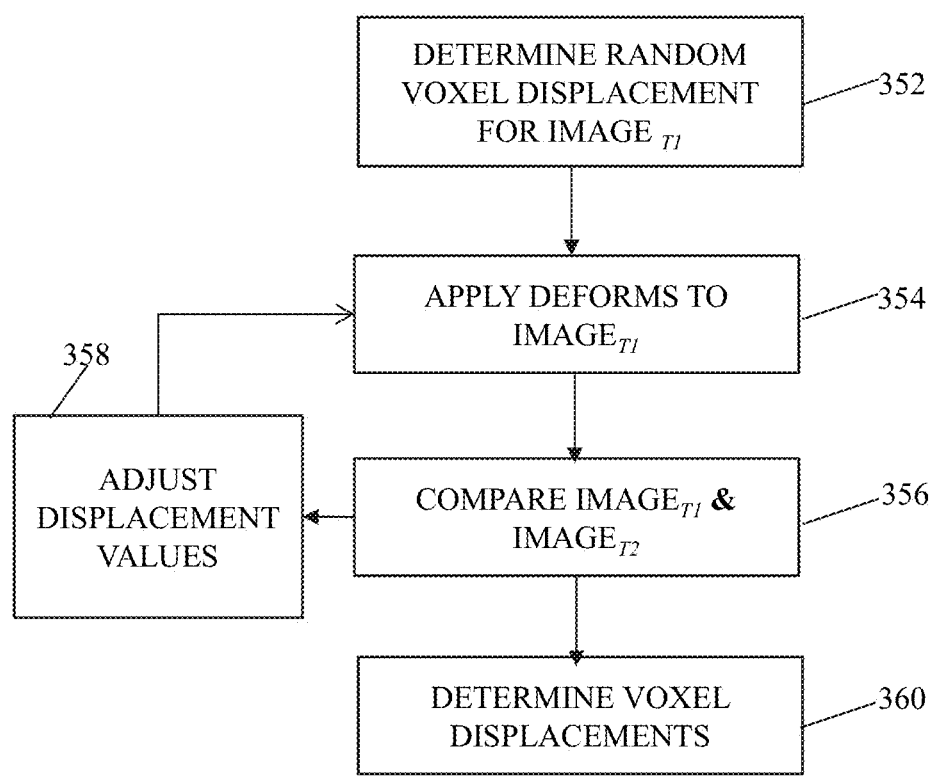

As shown in FIG. 3C, the method 350 may include a step 352 of assigning random values in voxel displacements and proceeds iteratively varying them. Next, the method 350 may include a step 354 of applying the displacements to one of the images to warp it to the second one. For example, the displacements on the pre-treatment image to warp the pre-treatment image to the second pre-treatment image. The method 350 may also include a step 356 of comparing the images to determine the results. For example, the anatomy shown in the pre-treatment image can be compared to the anatomy shown in the post-treatment image.

Next, based on the comparing step 356, the method 350 may include a step 358 of adjusting the values for the voxel displacements or may include a step 360 of determining voxel displacements.

If the comparing step 356 determines existing discrepancies between the images, the method 350 may subsequently include a step 358 of adjusting the voxel displacement values. The method 350 may then repeat steps 354 and 356. In some embodiments, steps 354-358 may be repeated until the comparing step 356 determines that existing errors are below a user-defined threshold or when a pre-set number of iterations has been reached.

If the comparing step 356 determines that the errors are above the threshold, the method may include a step 360 of determining new voxel displacement values that further minimize the differences. In some embodiments, the method 330 may include a step 338 of quantifying the voxel displacements. In some embodiments, step 338 may be omitted. In step 338, the changes in each image location can be quantified by the displacements found in 358. This can be stored for further processing, for example, for determining sum distribution and/or treatment response (e.g., FIGS. 6 and 8 (e.g., 620 or 820).

The method 330 may include a step 340 of aligning the images 332 and 334 based on the voxel displacements determined in step 360 (FIG. 3C).

Figure 4:
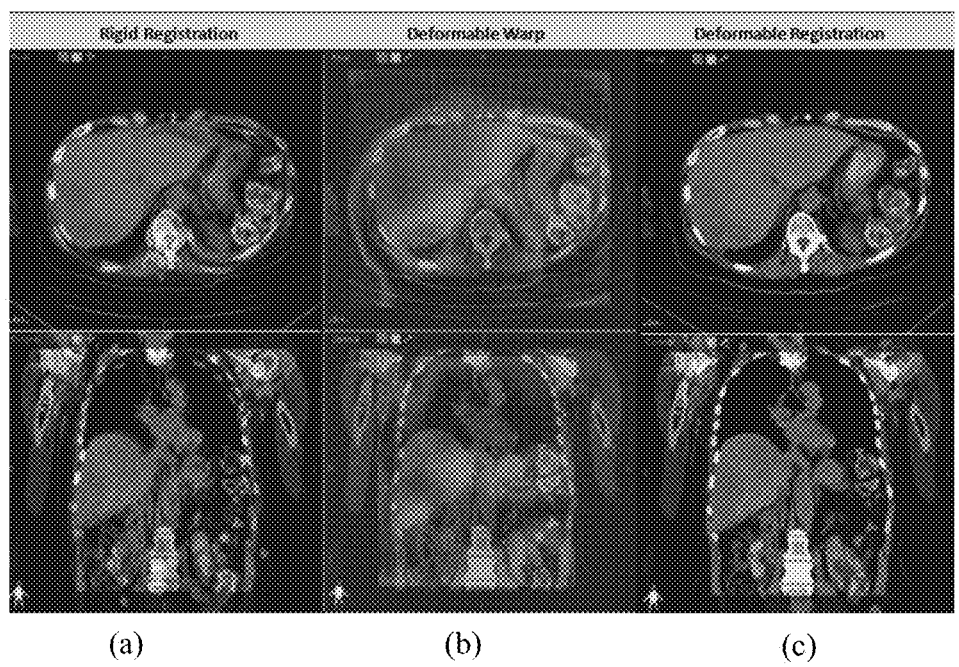
FIG. 4 shows an example of deformable registration according to some embodiments.

According to the disclosure, the deformable registration can automatically compensate for the differences between the images by creating per-voxel warping that corrected anatomical changes. FIGS. 4(*a*)-(*c*) show an example of the accuracy of deformable registration according to the disclosure. FIG. 4(*a*) shows two CT images registered with rigid registration can be misaligned. FIGS. 4(*b*) and (*c*) show the deformable warp and deformable registration of these two CT images, respectively. These figures show that the misalignments have been corrected for a more accurate registration through deformable warp.

The method 100 may include a step 130 of processing the registered image data (for example, according to FIGS. 2-3C) to determine a treatment response. The analysis may be based on at least, in part, the dose calculation (e.g., determined in step 122), the registered image data (e.g., determined in step 124), information from the treatment plan (e.g., planning dose, and/or planning contours), among others, and/or a combination thereof.

Figure 6:
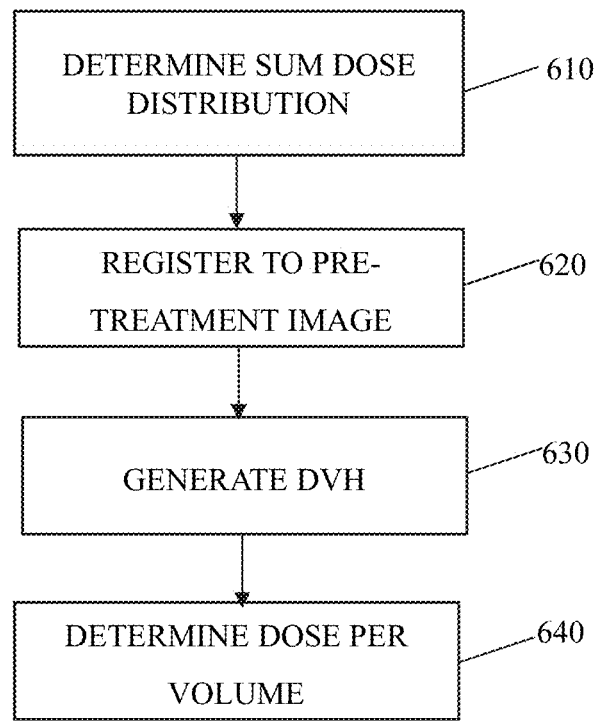
FIG. 6 shows a method of determining a sum dose distribution according to some embodiments.

FIG. 6 shows a method 600 of determining a treatment response based, at least in part, on dose calculations according to embodiments.

In some embodiments, the method 600 may include a step 610 of determining a sum dose distribution, for example, for the received image data. In some embodiments, the dose determined in step 122 for the image data for each time point may be processed during the registration step 124 to create a sum dose distribution file that does not include motion or posture changes occurring between the scans. For example, for image data that includes image data for two different treatment stages (e.g., pre-treatment and post-treatment stages), may be summed by registering, using deformable registration, the pre-treatment dataset to the post-treatment dataset to determine posture changes. These posture changes can be eliminated by resampling the pre-treatment dataset with the result of the deformable registration to create a one-to-one voxel correspondence between the pre and post treatment dataset. This one-to-one correspondence can be used to determine how voxels have been displaced between the scans. These displacements can be produced from the changes in patient's position during scans, by respiratory motion, or by anatomical changes. Once these displacements are found, each voxel can be tracked in time as its trajectory is known from the deformable registration. By way of another example, for example, if the registered image data includes image data for two different time points (e.g., post-treatment planning stage), the sum dose distribution can be determined by adding the dose value associated with each voxel. For example, a dose value associated with a voxel in an image at one time point can be summed with a dose value associated with the corresponding voxel in the other image at the different time point to determine the sum dose distribution. In other embodiments, other sum dose distribution methods may be used, for example, by tracking the voxel along it's trajectory in time and recording the dose received from different treatments delivered at different time points.

Figure 7:
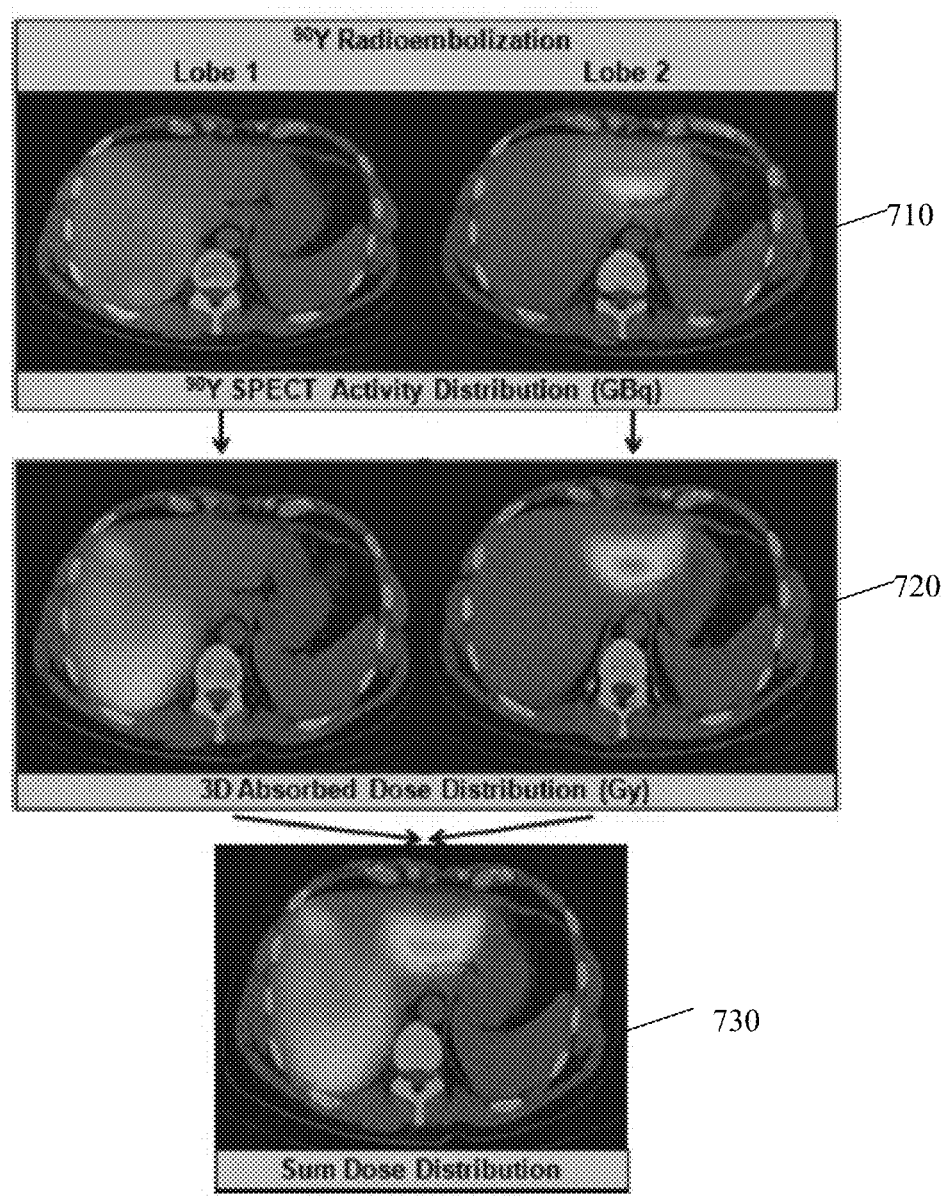
FIG. 7 shows an example of sum dose distribution according to some embodiments.

By way of example, FIG. 7 shows an example 700 where radioembolization was performed to each liver lobe in 2 staged procedures (710). In this example, the dose calculation (e.g., 3D dose distribution) was performed for each $^{90}$Y SPECT/CT data set (720) and the two image studies were then fused through deformable image registration according to FIGS. 3B and 3C, to generate one composite a sum dose distribution file (730).

In some embodiments, the method 600 may include a step 620 of registering sum dose distribution to an image for a session. For example, the sum distribution can be registered during the pre-treatment (e.g., pre-treatment diagnostic imaging used for tumor volume definition). The dose and images acquired at the same time point are in the same coordinates, i.e., a one-to-one correspondence in each voxel exists between a image voxel and the dose associated with it. By the process described in FIGS. 3B and 3C, a correspondence in time can be established between different image sets, for example a voxel from the first acquired image can be tracked to the subsequent ones. Because the dose and image voxel are directly related, the same trajectory on the dose can be applied to track it across subsequent images.

In some embodiments, the method 600 may include a step 630 of generating dose-volume histogram(s) (DVH). The DVHs correspond to histograms (i.e. counts of the number of voxels having a specific dose value) and can be constructed statistical measures to evaluate clinical usefulness of a treatment plan. These DVHs can be constructed by counting all voxels having a dose above a value. In some embodiments, the DVHs can be generated to be displayed as graphs.

In some embodiments, the method 600 may determine minimum, mean, and maximum dose for each tumor volume and/or normal tissue of the region of interest (e.g., liver) using the generated DVH.

In some embodiments, the step 130 may include determining a treatment response for a patient based on one or more regions of classified voxels. In some embodiments, the treatment response may be determined according to the differences between classified voxels. For example, signal-enhancing region may indicate treatment failure (e.g., treatment-resistant region) and non-signal enhancing regions may indicate successful treatment (e.g., respondent region).

Figure 8A:
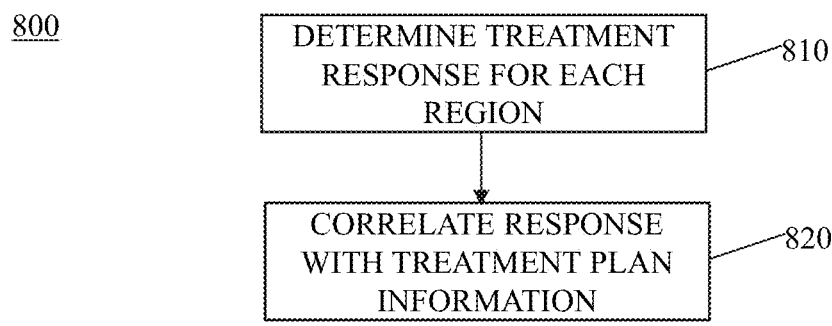
FIGS. 8A-8D show a method of determining a treatment response according to some embodiments.

FIG. 8A shows a method 800 for determining a treatment response based on voxel classification according to embodiments. In some embodiments, the method 800 may include a step 810 of determining a treatment response for each region. In some embodiments, the determining step 810 may be based on a segmentation method that evolves an initial estimate under the guidance of a level set equation to mark voxels into regions of signal reduction or amplification. The determining step 810 may be based on a level set approach that uses the location of the target volume to search only its vicinity for positive or negative changes to focus the analysis on clinically relevant regions. In other embodiments, concurrent algorithms such as statistical parameter mapping, support vector machine, or expectation maximization may also be used.

Figure 8B:
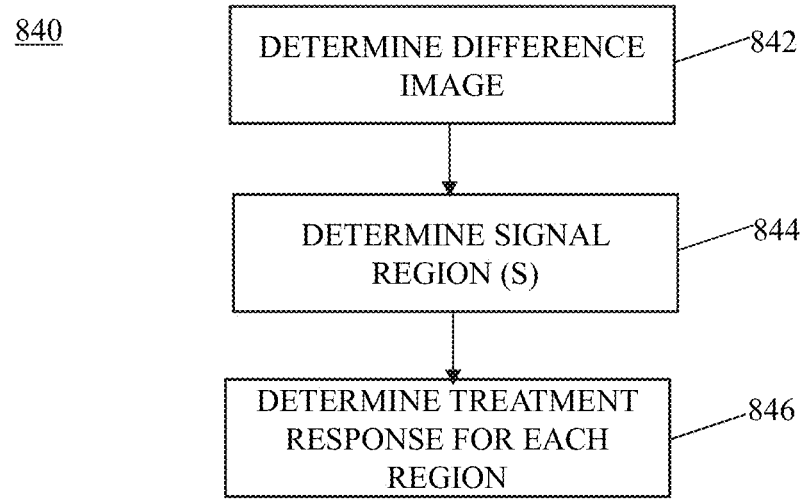

FIG. 8B shows a method 840 of determining a treatment response for each region. As shown in FIG. 8B, the method 840 may include a step of 842 of determining a difference image. In some embodiments, the difference image may be determined by subtracting the registered images to produce an image of molecular changes and embedded with noise.

Figure 8C:
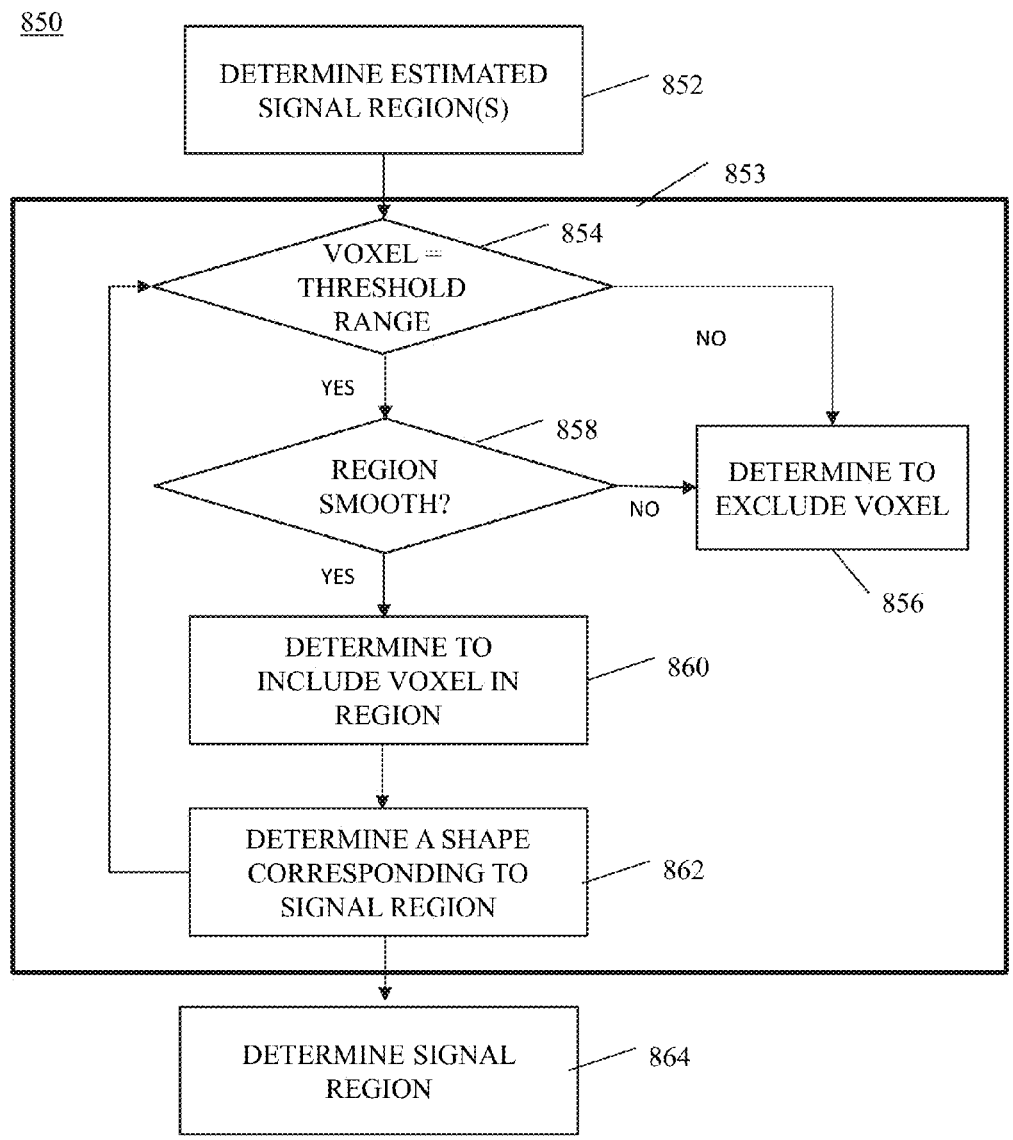

Next, the method 840 may include a step 844 of determining signal region(s). A signal region may be a region of one or more voxels that are grouped together based on location and signal value (also referred to as "blob regions.") The signal regions may be determined according to classified voxels and/or location with respect to a treatment site (e.g., a site that received a treatment dose and/or tumor location). FIG. 8C shows a method 850 of determining signal region(s), according to embodiments.

The equation controlling the evolution of the level set may be composed of two terms:

$$\partial A(x)/\partial t = [w_p P(x) + w_c C(x)]\nabla A(x),$$

where P(x) and C(x) denote terms constructed from image intensity and cluster shape at location x to control the propagation and curvature of the initial (or estimate) region or blob region (level set surface) A(x). The wp and wc are importance factors for each of the two terms and can be practically selected to influence algorithmic evolution. For example, the wp and wc can have values of 10 and 1, respectively.

The propagation term (Px) seeks to modify the cluster shape to include or exclude voxels whose intensities fall inside a specific threshold value range. The term P(x) can be defined as:

if $$I(x) < L + (U-L)/2,$$

then $$P(x) = I(x) - L$$

otherwise $$P(x) = U - I(x),$$

where I(x) is the voxel intensity at location x, and L and U are respectively lower and upper user specified thresholds of the standardized uptake (SUV) values being sought. If plotted, P(x) is a linear function that has a maximum at the middle of the (L, U) interval, L+(U−L)/2, decreasing to zero when the intensity I(x) reaches the lower or upper threshold, and having negative values outside the thresholds. Overall, the propagation term P(x) favors inclusion in the cluster of voxels with SUV values within the threshold interval (e.g., threshold range) and excludes voxels outside the threshold interval (e.g., threshold range).

The curvature term C(x) can contra balance the propagation term P(x) to minimize the inclusion of voxels that are affected by noise or where the feature sought is sporadic. For example, such voxels not belonging to the overall shape would appear as spikes protruding out of the shape. To minimize inclusion of such unwanted noise, the curvature can measure the surface curvature. The term can be defined as: $C(x)=\nabla*((\nabla A(x))/\|\nabla A(x)\|)$.

The fraction $((\nabla A(x))/\|\nabla A(x)\|)$ represents the vector normal to the blob surface A(x) at location x. Taking the gradient $\nabla$ of the surface normal is an effective approach to characterize smoothness, as small variations in the vector normal are expected if the surface is smooth.

In some embodiments, the method 850 may include a step 852 of determining estimated signal region(s). The estimated signal region(s) of one or more regions may correspond to blob regions determined from initial shapes. The initial shapes may be constructed automatically by thresholding the difference image to produce blob regions of signal changes. These regions may be then used as input for the clustering analysis (step 853), which can evolve the initial or estimate region until it matches clusters in the difference images. For example, nonenhancing regions that respond to treatment can be expected to display negative voxel values in the difference image and to be spatially located at a signal region or blob region, corresponding to the bulk tumor location. These voxels may be determined by thresholding the difference images, for example, to half the maximum negative value to estimate original tumor location. Enhancing clusters that mark tumor progression can be expected to have an increased signal value and can be located in the vicinity of the original tumor site. An initial estimate of them can be found by marking voxels with increased metabolic activity with an 10-mm isotropic margin from the treatment site.

Figure 8D:
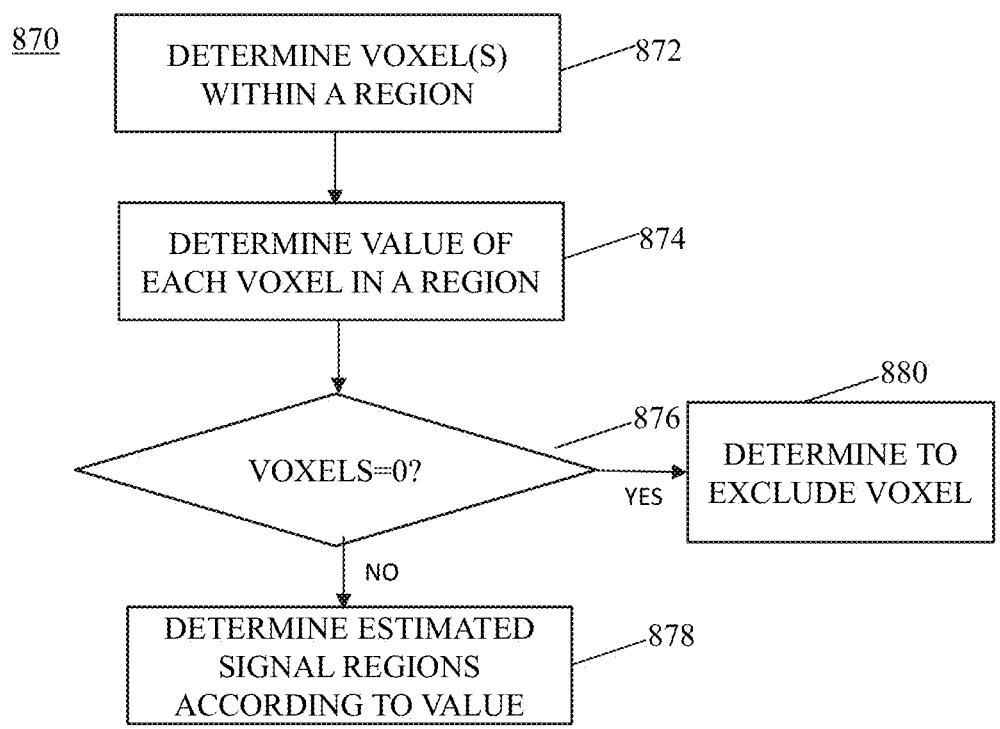

FIG. 8D shows a method 870 of determining an estimated signal region. As shown in FIG. 8D, the method 870 may include a step 872 of determining voxels within a region with respect to a treatment site. For example, at least one grouping of one or more voxels may be determined from the difference images that are within an area of a treatment site (e.g., a site that received a dose and/or tumor). The step 872 may include comparing the difference images and the dose (from the treatment plan) to a determine one or more treatment sites. Then, the step 872 may include determining a group of one or more voxels surrounding the treatment site that meet a threshold value. For example, one or more voxels within a threshold of about 1 cm-2 cm surrounding a treatment site may be determined to be included in the group. The threshold is not limited to those values and may be of any values. The region may include the one or more voxels that are grouped together based on location and signal value (also referred to as "blob regions.")

In some embodiments, the method 870 may include a step 874 of determining a value of each voxel in that region. For example, the step 874 may determine whether the values are negative (e.g., equal and/or below about −0.1), positive (e.g., equal and/or above about +0.1), are 0 (e.g., equal to about 0). If the step 874 determines that the value of a voxel equals about 0 (YES at step 876), then the method 870 may determine to exclude the voxel (step 880). For the values that are either positive and/or negative, the method 870 may determine estimate signal regions according to the either negative or positive value (step 878). In this way, for each difference image, there may be one or more estimated signal regions of one or more voxels that are grouped together based on location with respect to the treatment site and signal value. The step 878 can result in one or more estimated signal regions having a negative value (for example, which corresponds to estimated nonenhancing region(s)) and one or more estimated signal regions having a positive value (for example, which corresponds to estimated enhancing region(s)).

Next, the method 850 may include inputting each signal region (e.g., each enhancing and/or nonenhancing region) into the clustering analysis 838 to determine the signal regions to be evaluated for treatment response. In some embodiments, the clustering analysis 853 of the estimated signal region(s) may include comparing an intensity each voxel of that region to the threshold range of SUV values (step 854) and determining the smoothness associated with the value (step 858). The threshold range may depend on the signal value of the region (e.g., positive and/or negative). In this way, the threshold range may be different for the positive and negative value regions.

In some embodiments, the threshold range may be based on the voxel values included in the registered image. For example, from the estimated or initial signal region(s), the maximum negative and positive values, which respectively correspond to the minimum and maximum values in the difference image, for the pixels provided in each estimated signal region may be determined. By way of example, for a negative signal region, the threshold range or interval may correspond to the determined minimum value in the signal region to about −0.1; and for a positive signal region, the threshold range or interval may correspond to about 0.1 to the determined maximum value. In other embodiments, the threshold range or interval may be determined to according to different methods and/or set values.

If the value is outside the threshold range (NO at step 854), then it is determined to exclude the voxel (step 856) from the refined region and/or blob shape. If the value is within the threshold range (YES at 854), then the method 850, for example, in conjunction with step 854, may determine whether the voxel maintains the smoothness (e.g., step 858). For example, if the voxel is determined to be within the threshold, the method may also then evaluate one or more voxels surrounding that voxel to determine whether it is an outlier (e.g., resulting from noise). In this way, the method can evaluate the values associated with the one or more voxels surrounding that voxel to determine whether the value of that voxel is consistent with the neighboring voxel(s). This ensures that the region is smooth and that the neighboring voxels appear be consistent.

If the voxel is determined to be outlier (e.g., inconsistent with the neighboring voxel(s)) (NO at step 858), then the voxel can be determined to be excluded (step 856). In step 856, if the voxel is determined to be consistent with neighboring voxel(s) (YES at step 858), then the voxel can be determined to be included in the signal region or blob. Next, the cluster shape corresponding to the signal region may be determined (step 862).

Steps 854-862 can be repeated for each voxel in the region. In some embodiments, steps 854-862 for each region may be repeated until predetermined settings are reached. For example, the settings may include but is not limited to a certain root mean square error change and/or number of interactions. For example, the weighting factor terms may be about −10 for propagation, and 1 for curvature. By way of example, steps 854-862 may be determined to step when about 1000 iterations are reached or when the root mean square error change in the level set function is below about 10e-5. In some embodiments, the settings may have different values.

Next, after the steps 854-862 have been repeated for each voxel and/or according to the settings, the method 850 may include a step 864 of determining a signal region.

As shown in FIG. 8B, the method 840 may include a step of determining a treatment response for each region based on the associated signal value. For example, a region with positive or increased voxel values may indicate a treatment-resistant region (e.g., poor treatment response). Poor treatment response may be associated with variations in individual biological response and/or geographical errors. In another example, a signal region associated negative or decreased voxel values may indicate a respondent region (e.g., successful treatment response).

Next, in step, the treatment response for each region may be correlated with treatment plan information. The treatment plan information may include but is not limited to planning dose, planning contours, sum dose distribution, among others, or a combination thereof. For example, a region that includes one or more voxels marked by the clustering algorithm as corresponding to a signal increase (positive values) may be shown in relation to the target and delivered dose, with standard dose-volume histogram (DVH) tools employed to measure delivered dose and deviation from prescription in those regions. Enhancing regions inside the original target volume that received high levels of radiation may be attributed to poor tumor response (e.g., due to variations in individual biological response).

In some embodiments, geographical errors (e.g., regions of poor response near tumor margins) may be determined and may be outputted to the user (e.g., for a more in-depth analysis of the cause). These regions may be identified as possible treatment errors. These errors may be provided on a generated report or a colored map superimposed on the original plan. In some embodiments, the method may determine geographical errors based on the signal values and location with respect to original tumor site. For example, region(s) of positive values (signal increase) (e.g., determined in FIG. 8C) that are generally spatially located near an original tumor site may be determined to geographical error(s).

In some embodiments, the method 100 may include a step 140 of outputting the results. The results may include at least one of a report, a visual map, etc., or a combination thereof. The results, for example, may include the treatment response (e.g., enhancing and nonenhancing regions, as well their location and size) and/or correlated response determined in FIG. 8A with treatment plan information. The results may include tumor volume definition, sum dose distribution (e.g., determined in FIG. 6 (e.g., registered to one the images (e.g., pre-treatment diagnostic imaging for tumor volume definition)), dose-volume histograms, or a combination thereof. In some embodiments, the results can be saved in formats specific to statistical analysis software for population-based analysis of treatment outcomes under particular regimens. In some embodiments, the outputting may include but is not limited to displaying the registered image(s) with the treatment response and/or correlated treatment plan information, printing the image(s), and storing the image(s) remotely or locally. In other embodiments, the image(s) may be forwarded for further processing.

In some embodiments, the method may further include transmitting the generated image to another system. In some embodiments, the method may further include transmitting the generated image to an image-guided therapy delivery device. The image-guided therapy device may be any device configured to deliver drug therapy (e.g., chemotherapy and/or radiotherapy).

System

Figure 5:
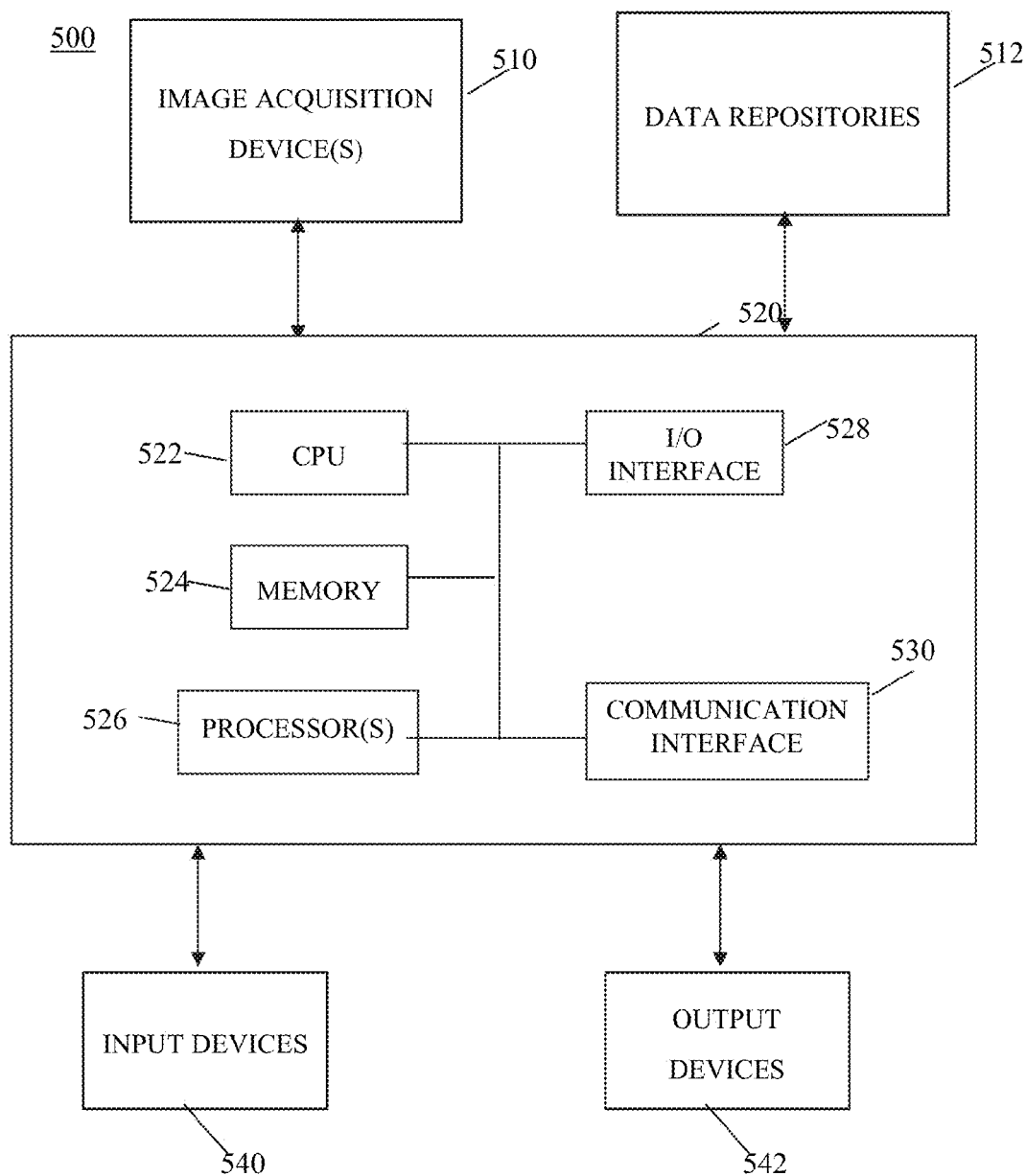
FIG. 5 shows a system configured for treatment planning and determine treatment response.

FIG. 5 shows an example of a system 500 for treatment planning and treatment assessment. The system for carrying out the embodiments of the methods (e.g., FIGS. 1-3C, 6, and 8A-8D) disclosed herein is not limited to the system shown in FIG. 5. Other systems may be used.

In some embodiments, the system 500 may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

Although the modules of the system are shown as being directly connected, the modules may be indirectly connected to one or more of the other modules of the system. In some embodiments, a module may be only directly connected to one or more of the other modules of the system.

It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the system may be time synchronized. In further embodiments, the system may be time synchronized with other systems, such as those systems that may be on the medical facility network.

In some embodiments, the system 500 may include at least one image acquisition device 510 configured to acquire the image data of a subject. The image acquisition device(s) 510 may be any device configured to generate and acquire images. The device(s) 510 may include but is not limited to CT, SPECT, MRI, PET, or a combination thereof. In other embodiments, the system 500 may communicate with the imaging systems and/or a data storage device. For example, the system may include one or more data repositories 512, such as a radiological image storage (e.g., Picture Archiving and Communication System (PACS)).

In some embodiments, the image acquisition device 510 may include a computer system to carry out the image processing. The computer system may further be used to control the operation of the system or a separate system may be included.

The system 500 may include a system 520 to carry out the image processing to determine a treatment response, according to embodiments. In some embodiments, the system 520 may be a separate device. In other embodiments, the system 520 may be a part (e.g., stored on the memory) of other modules, (for example, the image acquisition device 510, an image-guided dosimetry system, among others, or a combination thereof) and controlled by its respective CPUs, The system 520 may further be used to control the operation of the image acquisition device 510 or an image-guided dosimetry system, or a computer separate system may be included.

The system 520 may also be connected to another computer system as well as a wired or wireless network. The system 520 may receive or obtain the image data from the image acquisition device(s) 510 or from another module, such as a hospital server provided on a network.

The system 520 may be a computing system, such as a workstation, computer, or the like. The system 520 may include one or more processors 522. The processor(s) 522 (also referred to as central processing units, or CPUs) may be any known central processing unit, a processor, or a microprocessor. The CPU 522 may be coupled directly or indirectly to one or more computer-readable storage media (e.g., memory) 524. The memory 524 may include random access memory (RAM), read only memory (ROM), disk drive, tape drive, etc., or a combinations thereof. The memory may also include a frame buffer for storing image data arrays. The CPU 522 may be configured to control the image acquisition, image-guided therapy, and/or process the acquired images, for example, to determine a treatment response according to embodiments. In some embodiments, the CPU 522 may be capable of performing the image processing functionality. In other embodiments, the system may include a separate CPU for performing the image processing functionality.

In some embodiments, the CPU 522 may be configured to process the image data acquired from the image acquisition device 510. In some embodiments, the system 500 may include one or more image processors 526 (e.g., any known processing unit such as a CPU, a processor, or a microprocessor) configured to process raw image data. The processed data and results may then be stored in the memory 524. In some embodiments, another computer system may assume the image analysis or other functions of the CPU 522 or image processor 526. In response to commands received from the input device, the image data stored in the memory 524 may be archived in long term storage or may be further processed by the image processor and presented on a display.

In some embodiments, the disclosed methods (e.g., FIGS. 1-3C, 6, and 8A-8D) may be implemented using software applications that are stored in a memory and executed by a processor (e.g., CPU) provided on the system. In some embodiments, the disclosed methods may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system. In addition, various other peripheral devices may be connected to the computer platform such as an additional data storage device, a printing device, and other I/O (input/output) devices.

In some embodiments, the system 520 may include a communication interface 530 configured to conduct receiving and transmitting of data between other modules on the system and/or network. The communication interface 530 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 500 may include an input/output interface 528 configured for receiving information from one or more input devices 540 (e.g., a keyboard, a mouse, and the like) and/or conveying information to one or more output devices 542 (e.g., a printer, a CD writer, a DVD writer, portable flash memory, etc.). In some embodiments, the one or more input devices 540 may configured to control the generation of the images, display of images on a display, and/or printing of the images by a printer interface.

It is to be understood that the embodiments of the disclosure be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for determining a treatment response of a treatment for a region of interest, comprising:

registering at least a first image data and a second image data of a region of interest to generate a registered image, the first image data corresponding to a first time point, the second image data corresponding to a second time point, the first time point and the second time point being different with respect to a session and/or treatment stage;

determining a treatment response, by a computer having a processor and a memory, based on at least the registered image, treatment plan information associated with the treatment, or a combination thereof, the determining including:

processing the registered image to determine a difference image;

processing at least the difference image to determine one or more signal regions, each signal region corresponding to one or more voxels that are grouped together based on location and signal value, the one or more signal regions including a positive signal region and/or a negative signal region; and determining a treatment response for each signal region based on the signal value associated with the each region, the positive signal region indicating a treatment-resistant region and the negative signal region indicating a respondent region; and outputting treatment response results, the treatment response results including the treatment response.

2. The method according to claim 1, wherein the processing at least the difference image to determine one or more signal regions include:

determining an estimate signal region of one or more voxels based on the signal value and location with respect to a treatment site; and processing each voxel of the estimate signal region to determine the signal region, the processing including comparing each voxel to a threshold range associated with the signal value and estimated signal region.

3. The method according to claim 2, wherein the processing each voxel of the estimate signal region to determine the signal region includes:

determining to include a voxel in the signal region when a signal value of the voxel is within the threshold range and is consistent with a signal value of one or more voxels neighboring the each voxel, and determining to exclude a voxel from the signal region when a value of the voxel is outside the threshold, the value of the voxel is inconsistent with a signal value of one or more voxels neighboring the each voxel, or a combination thereof.

4. The method according to claim 1, wherein the treatment stage includes pre-treatment, pre-treatment planning, post-treatment planning, post-treatment, or a combination thereof.

5. The method according to claim 1, wherein the image data for each time point includes PET, MR, CT, SPECT-CT, or a combination thereof.

6. The method according to claim 1, further comprising:
correlating the treatment response for each region with the treatment plan information;
wherein the treatment response results includes the registered image with the one or more signal regions with the associated treatment response and the treatment plan information,
wherein the treatment plan information includes planning dose, planning contours, delivered dose, or a combination thereof.

7. The method according to claim 1, further comprising:
determining a dose for each image; and
correlating the dose with the one or more signal regions.

8. The method according to claim 1, further comprising:
determining a dose for each image; and
determining a sum distribution file based on the registered image.

9. The method according to claim 1, wherein the registration is deformable registration.

10. A method for determining a treatment response of a treatment for a region of interest, comprising:
registering at least a first image data and a second image data of a region of interest to generate a registered image, the first image data corresponding to a first time point, the second image data corresponding to a second time point, the first time point and the second time point being different with respect to a session and/or treatment stage;

determining a dose for each of voxel of the first image data and the second image data;

determining a treatment response, by a computer having a processor and a memory, based on at least the registered image, the determining including;

determining a sum dose distribution using the registered image by adding the dose associated with each voxel of the first image data to each corresponding voxel of the second image data;

classifying each voxel of the registered image into one or more signal regions based on signal value and/or location;

correlating the sum dose distribution to the one or more signal regions; and determining the treatment response based on the sum dose distribution; and outputting treatment response results that include the treatment response.

11. The method according to claim 10, further comprising:

generating a dose volume histogram from the dose, the sum dose distribution, or a combination thereof; and wherein the treatment response results includes the dose volume histogram.

12. The method according to claim 10,
wherein the classifying each voxel of the registered image includes:

processing the registered image to determine a difference image;

processing at least the difference image to determine the one or more signal regions, each signal region corresponding to one or more voxels that are grouped together based on the location and the signal value, the one or more signal regions including a positive signal region and/or a negative signal region; and determining the treatment response associated with the signal value of the one or more signal regions, the positive signal region indicating a treatment-resistant region and the negative signal region indicating a respondent region.

13. The method according to claim 12, wherein the processing at least the difference image to determine one or more signal regions include:

determining an estimate signal region of one or more voxels based on the signal value and location with respect to a treatment site; and processing each voxel of the estimate signal region to determine the signal region, the processing including comparing each voxel to a threshold range associated with the signal value and estimated signal region.

14. The method according to claim 13, wherein the processing each voxel of the estimate signal region to determine the signal region includes:

determining to include a voxel in the signal region when a signal value of the voxel is within the threshold range and is consistent with a signal value of one or more voxels neighboring the each voxel, and determining to exclude a voxel from the signal region when a value of the voxel is outside the threshold, the value of the voxel is inconsistent with a signal value of one or more voxels neighboring the each voxel, or a combination thereof.

15. The method according to claim 10, wherein the treatment stage includes pre-treatment, pre-treatment planning, post-treatment planning, post-treatment, or a combination thereof.

16. The method according to claim 10, wherein the image data for each time point includes PET, MR, CT, SPECT-CT, or a combination thereof.

17. The method according to claim 10, wherein the registration is deformable registration.

18. The method according to claim 10, wherein the sum dose distribution is determined from PET data.

19. A non-transitory computer-readable storage medium storing instructions for determining a treatment response of a treatment for a region of interest, the instructions comprising:

registering at least a first image data and a second image data of a region of interest to generate a registered image, the first image data corresponding to a first time point, the second image data corresponding to a second time point, the first time point and the second time point being different with respect to a session and/or treatment stage;

determining a dose for each of voxel of the first image data and the second image data;

determining a treatment response, by a computer having a processor and a memory, based on at least the registered image, the determining including;

determining a sum dose distribution using the registered image by adding the dose associated with each voxel of the first image data to each corresponding voxel of the second image data;

classifying each voxel of the registered image into one or more signal regions based on signal value and/or location;

correlating the sum dose distribution to the one or more signal regions; and determining the treatment response based on the sum dose distribution; and outputting treatment response results that include the treatment response.

20. The computer-readable storage medium according to claim 19, the instructions further comprising:

generating a dose volume histogram from the dose, the sum dose distribution, or a combination thereof; and wherein the treatment response results includes the dose volume histogram.

\* \* \* \* \*